United States Patent
Ieda et al.

(10) Patent No.: US 8,268,147 B2
(45) Date of Patent: Sep. 18, 2012

(54) GAS SENSOR CONTROL DEVICE AND METHOD

(75) Inventors: Norikazu Ieda, Nagoya (JP); Tomonori Uemura, Nagoya (JP); Hiroshi Inagaki, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1181 days.

(21) Appl. No.: 11/898,552

(22) Filed: Sep. 13, 2007

(65) Prior Publication Data

US 2008/0060941 A1 Mar. 13, 2008

(30) Foreign Application Priority Data

Sep. 13, 2006 (JP) .................. 2006-248100

(51) Int. Cl.
*G01N 27/419* (2006.01)
*G01N 27/26* (2006.01)
*G06F 19/00* (2011.01)

(52) U.S. Cl. ...... 204/431; 73/23.31; 73/23.32; 324/537; 123/688; 700/114; 700/109; 204/424; 204/401

(58) Field of Classification Search .......... 204/421–429, 204/410, 411; 73/23.32, 23.31; 701/114, 701/109; 123/688; 324/537

See application file for complete search history.

(56) References Cited

U.S. PATENT DOCUMENTS

| 6,567,738 B2 * | 5/2003 | Gopp et al. ............ 701/109 |
| 2004/0026408 A1 * | 2/2004 | Morinaga et al. ........ 219/497 |
| 2005/0029098 A1 * | 2/2005 | Aoki et al. ............. 204/406 |
| 2005/0288847 A1 * | 12/2005 | Inoue et al. ............ 701/114 |
| 2006/0157348 A1 * | 7/2006 | Inoue et al. ............ 204/401 |

FOREIGN PATENT DOCUMENTS

JP 2003-90821 3/2003

* cited by examiner

*Primary Examiner* — Jeffrey T Barton
*Assistant Examiner* — Jennifer Dieterle
(74) *Attorney, Agent, or Firm* — Sughrue Mion, PLLC (57) ABSTRACT

A control device for a gas sensor is configured to: receive a mode command to specify one of a plurality of sensor energization modes including at least a gas concentration detection mode, a protection mode and a pre-energization mode; switch a sensor element of the gas sensor into the one of the plurality of sensor energization modes according to the mode command; judge satisfaction of a certain condition where the mode command is to specify the gas concentration detection mode and the sensor element is in any of the plurality of sensor energization modes other than the pre-energization mode at the time of receipt of the mode command; and prohibit the sensor element from switching over to the gas concentration detection mode when the certain condition is satisfied.

10 Claims, 4 Drawing Sheets

| MODE | SWITCH | | | | |
|---|---|---|---|---|---|
| | SW1 | SW2 | SW3 | SW4 | SW5 |
| GAS CONCENTRATION DETECTION MODE | OFF | ON | ON | OFF | ON |
| PROTECTION MODE | OFF | OFF | OFF | OFF | OFF |
| PRE-ENERGIZATION MODE | ON | OFF | OFF | ON | ON |

FIG.4

GAS SENSOR CONTROL DEVICE AND METHOD

BACKGROUND OF THE INVENTION

The present invention relates to a gas sensor control device and method.

As a combustion control technique for reduction of CO, NOx and HC exhaust emissions from internal combustion engine e.g. gasoline engine, air-fuel ratio feedback control is widely used to regulate fuel injection in accordance with the concentration of a specific gas component in engine exhaust gas.

There are various exhaust gas sensors for use in the air-fuel ratio control. One example of exhaust gas sensor is an oxygen sensor having a single electrochemical cell in which a solid electrolyte material body is arranged between electrodes to detect the concentration of oxygen in measurement exhaust gas. Another example of exhaust gas sensor is an air-fuel ratio sensor (also called a "universal exhaust gas oxygen sensor") having two electrochemical cells: a sensing cell and a pumping cell with a measurement gas chamber defined between these electrochemical cells to introduce measurement exhaust gas into the measurement gas chamber through a gas diffusion material and detect the concentration of oxygen in the measurement exhaust gas. A NOx sensor with three electrochemical cells is also known as exhaust gas sensor.

Japanese Laid-Open Patent Publication No. 2003090821 discloses one type of sensor control device that controls energization of the exhaust gas sensor, and more specifically, the sensor cell or cells. In general, the sensor control device provides a plurality of sensor energization modes such as a gas concentration detection mode, a protection mode and a pre-energization mode. The gas concentration detection mode is selected to energize the gas sensor with a relatively large electric current for gas concentration detection. The protection mode is selected to interrupt electrical continuity between the gas sensor and the sensor control device for electrical protection of the gas sensor. The pre-energization mode is selected to pre-energize the gas sensor with a small electric current and thereby activate the gas sensor in readiness for the gas concentration detection mode.

SUMMARY OF THE INVENTION

In the event of a sensor connection failure e.g. a short circuit, however, there arises an excessive current flow through the gas sensor when the sensor control device switches the gas sensor directly into the gas concentration detection mode. The gas sensor sustains damage called "cell blackening" etc. due to such an excessive current flow.

It is therefore an object of the present invention to provide a device and method for controlling energization of a gas sensor without causing sensor damage in the event of a sensor connection failure.

According to a first aspect of the present invention, there is provided a control device for a gas sensor, the gas sensor having a sensor element formed with at least one electrochemical cell to detect the concentration of a specific gas component in measurement gas, the control device being configured to: receive a mode command to specify one of a plurality of sensor energization modes including at least a gas concentration detection mode, a protection mode and a pre-energization mode; switch the sensor element into the one of the plurality of sensor energization modes according to the mode command; judge satisfaction of a certain condition where the mode command is to specify the gas concentration detection mode and the sensor element is in any of the plurality of sensor energization modes other than the pre-energization mode at the time of receipt of the mode command; and prohibit the sensor element from switching over to the gas concentration detection mode when the certain condition is satisfied.

According to a second aspect of the present invention, there is provided a gas sensor system, comprising: a gas sensor having a sensor element formed with at least one electrochemical cell to detect the concentration of a specific gas component in measurement gas; and a control device having means for controlling energization of the sensor element in a plurality of energization modes including at least a gas concentration detection mode, a protection mode and a pre-energization mode and means for prohibiting a switchover of the sensor element from any of the energization modes other than the pre-energization mode to the gas concentration detection mode.

According to a third aspect of the present invention, there is provided a control method for a gas sensor, the gas sensor having a sensor element formed with at least one electrochemical cell to detect the concentration of a specific gas component in measurement gas, the control method comprising: receiving a mode command to specify one of a plurality of sensor energization modes including at least a gas concentration detection mode, a protection mode and a pre-energization mode; switching the sensor element into the one of the plurality of sensor energization modes according to the mode command; judging satisfaction of a certain condition where the mode command is to specify the gas concentration detection mode and the sensor element is in any of the plurality of sensor energization modes other than the pre-energization mode at the time of receipt of the mode command; and prohibiting the sensor element from switching over to the gas concentration detection mode when the certain condition is satisfied.

The other objects and features of the present invention will also become understood from the following description.

DESCRIPTION OF THE EMBODIMENTS

The present invention will be described below with reference to the drawings.

Figure 1:
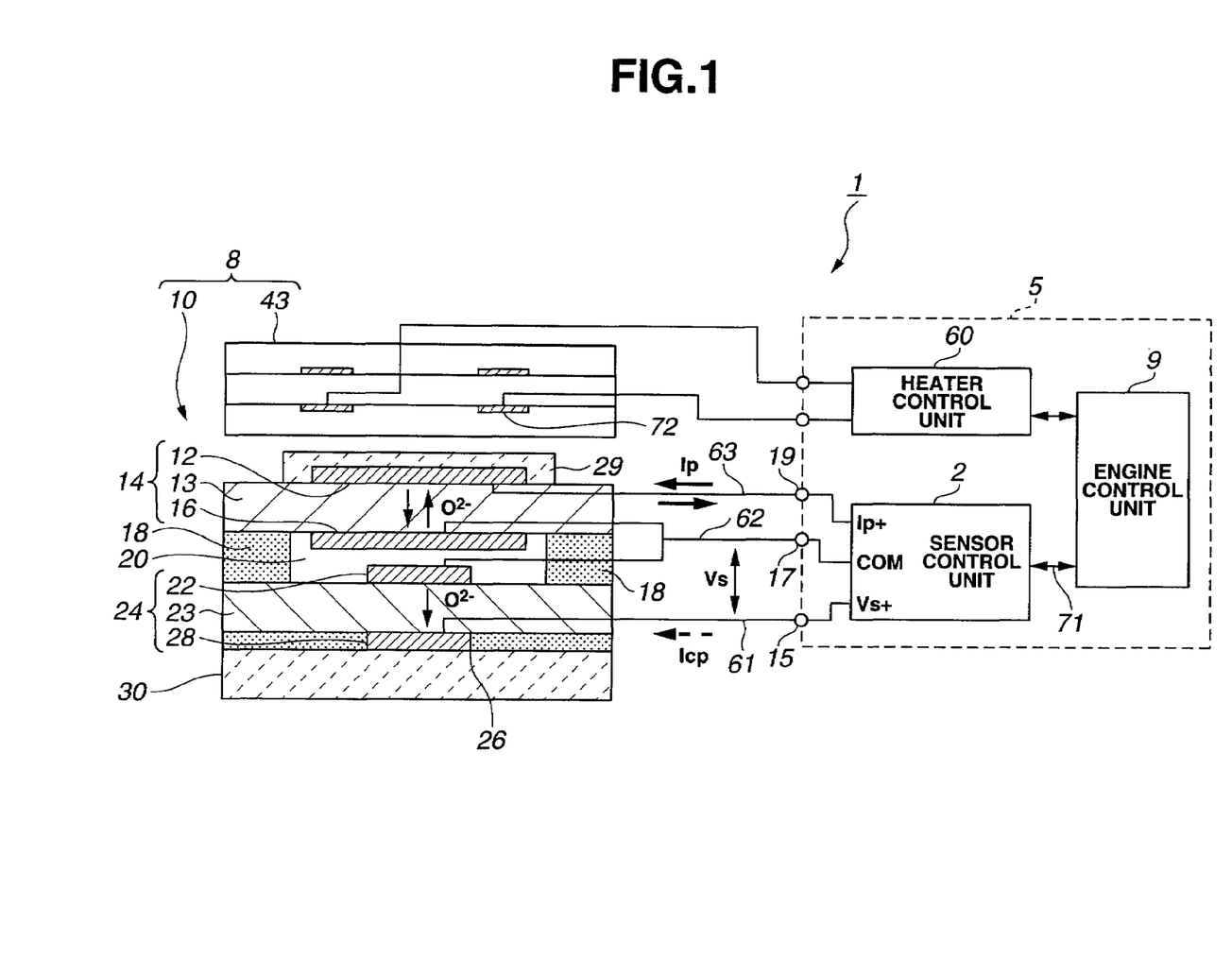
FIG. 1 is a schematic view of an engine control system with an exhaust gas sensor and an electronic control device according to one embodiment of the present invention.
Figure 2:
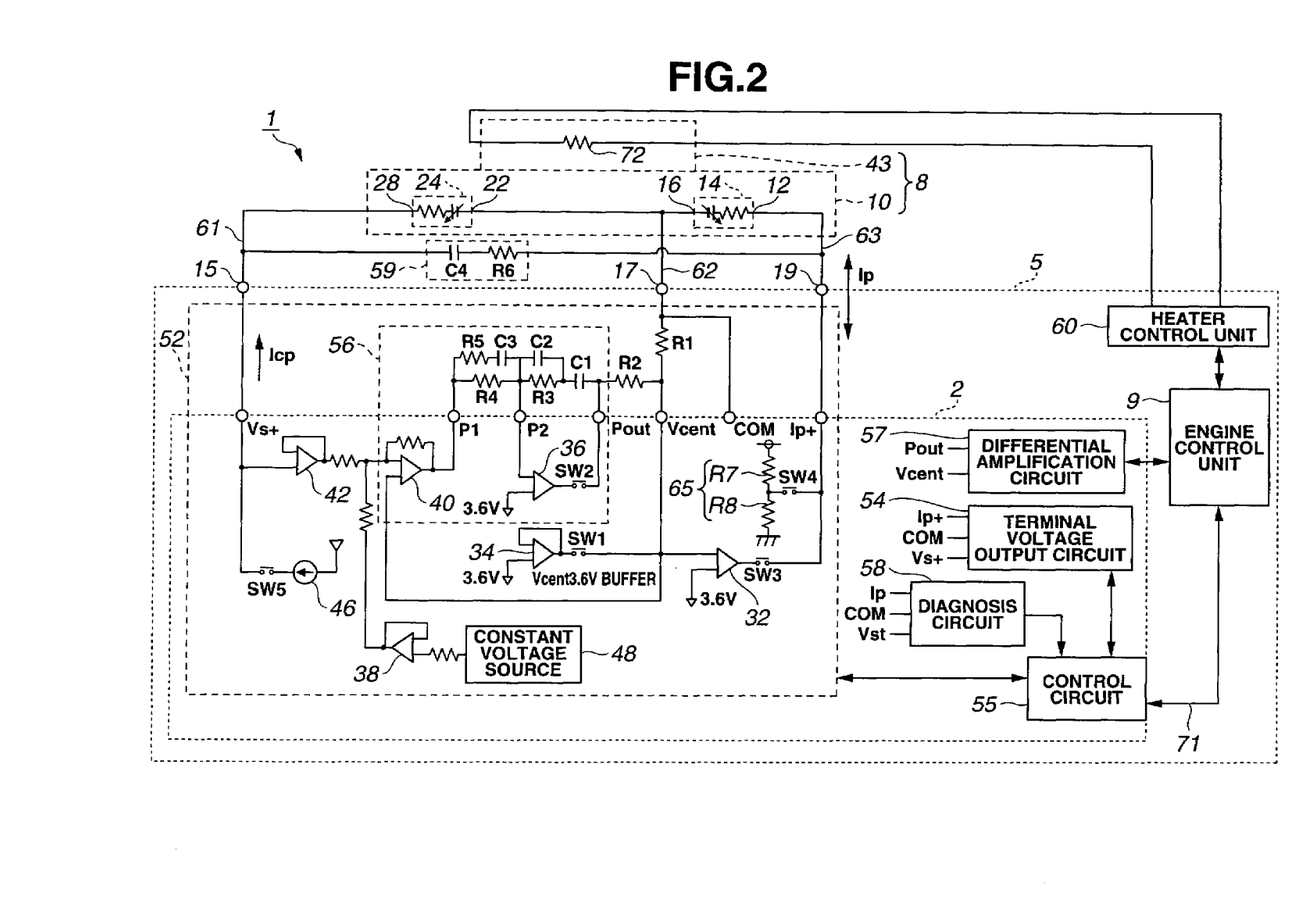
FIG. 2 is a circuit diagram of the electronic control device according to one embodiment of the present invention.

Referring to FIGS. 1 and 2, a control system 1 for an automotive internal combustion engine according to one exemplary embodiment of the present invention includes a gas sensor 8, an electronic control device 5 with a sensor control unit 2, an engine control unit 9 and a heater control unit 60, a signal transmission cable 71 and electric wires 61, 62 and 63.

The gas sensor 8 is mounted on an exhaust pipe of the engine and configured to produce an output according to the concentration of a specific gas component in engine exhaust gas. The gas sensor 8 can be of any type having at least one electrochemical cell such as a single-cell oxygen sensor, a two-cell air-fuel ratio sensor (also called a "universal exhaust gas oxygen sensor") or a three-cell NOx sensor. By way of example, the gas sensor 8 is a universal exhaust gas oxygen sensor in the present embodiment.

As shown in FIG. 1, the gas sensor 8 includes a sensor element 10 for outputting a current detection signal linearly responsive to the concentration of oxygen in the exhaust gas, and by extension, to the engine air-fuel ratio over a wide range and a heater 43 for activating the sensor element 10 by heating.

The sensor element 10 is equipped with a pumping cell 14, a sensing cell 24, a gas diffusion layer 18 and a reinforcing plate 30.

The pumping cell 14 has an oxygen-ion conductive solid electrolyte material body 13 and first and second electrodes 12 and 16. The solid electrolyte material body 13 is made of partially stabilized zirconia ($ZrO_2$) and formed into a plate shape. The first and second electrodes 12 and 16 are predominantly made of platinum (Pt), arranged on opposite sides of the solid electrolyte material body 13 and electrically connected to terminals 19 and 17 of the electronic control device 5 via the electric wires 63 and 62. Further, the first pumping cell electrode 12 is covered with a porous protection layer 29 to protect the pumping cell electrode 12 from any poisoning material.

The sensing cell 24 has an oxygen-ion conductive solid electrolyte material body 23 and first and second electrodes 22 and 28. The solid electrolyte material body 23 is also made of partially stabilized zirconia ($ZrO_2$) and formed into a plate shape. The first and second electrodes 22 and 28 are predominantly made of platinum (Pt), arranged on opposite sides of the solid electrolyte material body 23 and electrically connected to terminals 17 and 15 of the electronic control device 5 via the electric wires 62 and 61.

There is a hollow measurement gas chamber 20 defined between the pumping cell 14 and the sensing cell 24 with the second pumping cell electrode 16 and the first sensing cell electrode 22 being exposed to the measurement gas chamber 20 as shown in FIG. 1.

Although not shown in the drawings, an insulating layer is formed of e.g. alumina ($Al_2O_3$) between the pumping cell 14 and the sensing cell 24 such that these electrochemical cells 14 and 24 are electrically insulated from each other by the insulating layer.

The gas diffusion layer 18 is also formed between the pumping cell 14 and the sensing cell 24 so as to surround the measurement gas chamber 20 by the gas diffusion layer 18 and the insulating layer while allowing gas communication between the measurement gas chamber 20 and the outside of the sensor element 10 (measurement gas atmosphere) through the gas diffusion layer 18. In order to control the rate of diffusion of the measurement exhaust gas into the measurement gas chamber 20, the gas diffusion layer is made of a porous insulating material e.g. alumina ($Al_2O_3$). For gas diffusion rate control, gas diffusion pores may alternatively be formed instead of the porous gas diffusion layer 18.

The reinforcing plate 30 is attached externally to the sensing cell 24 so as to sandwich the second sensing cell electrode 28 between the solid electrolyte material body 23 and the reinforcing plate 30, with the sensing cell electrode 28 being separated from the outside of the sensor element 10 by the reinforcing plate 30, for improvement in the overall strength of the sensor element 10. In the present embodiment, the reinforcing plate 30 is substantially the same in size as the solid electrolyte material bodies 13 and 23 and is predominantly made of a ceramic material.

Further, there is a closed reference gas chamber 26 defined around the sensing cell electrode 28 between the sensing cell 24 and the reinforcing plate 30 as shown in FIG. 1.

The heater 43 is plate-shaped and located adjacent to the sensor element 10 with one side of the heater 43 facing the pumping cell 14. As shown in FIG. 1, the heater 43 has a heater body and an electrical wiring 72 arranged in the heater body and electrically connected at opposite ends thereof to the heater control unit 60. The heater body and the electrical wiring 72 are formed of e.g. alumina ($Al_2O_3$) and platinum (Pt), respectively. Under the control of the heater control unit 60, the heater 43 heats the sensor element 10 to an operating temperature of e.g. 550 to 900° C.

With the above sensor configuration, each of the pumping cell 14 and the sensing cell 24 enters an active state in which the solid electrolyte material body 13, 23 allows oxygen ion conduction when the sensor element 10 is kept at the operating temperature. During the active state, the pumping cell 14 performs its oxygen pumping action to cause pumping of oxygen in or out of the measurement gas chamber 20 by the passage of an electric current Ip from the sensor control unit 2 to the pumping cell 14. In view of the fact that the amount and direction of flow of the pumping cell current Ip varies depending on the exhaust oxygen concentration as will be explained later, the pumping cell current Ip is taken as the output signal of the sensor element 10. The sensing cell 24 also performs its oxygen pumping action during the active state and functions as a self-regulating reference electrode to accumulate a nearly constant concentration of oxygen as reference gas into the reference gas chamber 26 by the passage of a small constant current Icp (e.g. 17 μA) from the sensor control unit 2 to the sensing cell 24 in a direction from the second sensing cell electrode 28 to the first sensing cell electrode 22. As a result, there arises an electromotive voltage Vs across the sensing cell 24 according to a difference in oxygen concentrations between the measurement gas chamber 20 and the reference gas chamber 26. This electromotive voltage Vs of the sensing cell 24 is outputted as feedback to the sensor control unit 2.

The sensor control unit 2 controls the operations of the sensor element 10 (the energization of the pumping cell 14 and the sensing cell 24) while processing the current output Ip of the sensor element 10 into an oxygen concentration voltage signal. The sensor control unit 2 further detects an electrical resistance of the sensor element 10 and produces an output signal responsive to the detected resistance of the sensor element 10. Herein, the electrical resistance of the sensor element 10 can be detected by any known technique, e.g., by sampling and holding the output of the pumping cell 14 (or the sensing cell 24) with the periodical supply of a given amount of electric current (or voltage). A detail explanation of the resistance signal processing technique will be omitted for the sake of simplicity. As the sensor resistance varies with the sensor temperature, the sensor resistance signal is used as a parameter indicating the operating status of the sensor element 10. The oxygen concentration signal and the sensor resistance signal are outputted to the engine control unit 9.

As shown in FIG. 2, the sensor control unit 2 includes a drive circuit 52, a differential amplification circuit 57, a terminal voltage output circuit 54, a control circuit 55, an oscillation inhibiting circuit 59 and a diagnosis circuit 58.

The drive circuit 52 is comprised of operational amplifiers 32, 34, 36 and 42, a voltage divider 65, a PID controller 56, a constant voltage source 48, a constant current source 46, resistors R1 and R2 and mode selection switches SW1 to SW5 so as to perform drive control of the sensor cells 14 and 24.

Further, the drive circuit 52 is equipped with terminals Vs+, COM and Ip+. The circuit terminal Vs+ is electrically connected to the device terminal 15 so as to provide electrical continuity between the drive circuit 52 and the cell electrode 28 through the circuit terminal Vs+, the device terminal 15 and the electric wire 61 for the passage of the constant current Icp through the pumping cell 14. The circuit terminal COM is electrically connected to the device terminal 17 so as to provide electrical continuity between the drive circuit 2 and the cell electrodes 22 and 16 through the circuit terminal COM, the device terminal 17 and the electric wire 62 for the application of a common reference voltage to the pumping cell 14 and the sensing cell 24. The circuit terminal Ip+ is electrically connected to the device terminal 19 so as to provide electrical continuity between the drive circuit 52 and the cell electrode 12 through the circuit terminal Ip+, the device terminal 19 and the electric wire 63 for the passage of the electric current Ip through the sensing cell 24. The drive circuit 52 is also equipped with terminals P1 and P2 for external attachment of circuit components of the PID controller 56 as well as terminals Pout and Vcent for electrical connection to the sensor element 10 and the differential amplification circuit 57.

The operational amplifier 32 has an inverting input terminal connected to the PID controller 56 via the circuit terminal Vcent and the resistor R2, a noninverting input terminal connected to a reference voltage of 3.6 V and an output terminal connected to the circuit terminal Ip+ via the switch SW3, thereby forming a negative feedback loop to feed the pumping cell current Ip through the pumping cell 14 under the control of the PID controller 56. The output Ip of the operational amplifier 32 is turned on and off by the switch SW3.

The voltage divider 65 has resistors R7 and R8 to divide a constant power supply voltage in half. The junction of the resistors R7 and R8 is connected to the circuit terminal Ip+ via the switch SW4 so that the output of the voltage divider 65 is turned on and off by the switch SW4.

The PID controller 56 has operational amplifiers 36 and 40, resistors R3, R4 and R5 and capacitors C1, C2 and C3. The resistors R3, R4 and R5 and the capacitors C1, C2 and C3 are externally added to the terminals P1 and P2 so as to define control parameters of the PID controller 56. One input terminal of the PID controller 56 (i.e. the inverting input terminal of the operational amplifier 40) is connected to the circuit terminal Vs+ via the amplifier 42, whereas another input terminal of the PID controller 56 (i.e. the non-inverting input terminal of the operational amplifier 40) is connected to the constant voltage source 48 via the amplifier 38. The constant voltage source 48 supplies a control target voltage of 450 mV to the PID controller 56 as a control target value for control of the pumping cell current Ip. Accordingly, the PID controller 56 receives the output voltage Vs from the sensing cell 24 and the control target voltage from the constant voltage source 48 and performs PID operation on the difference ΔVs+ between the sensing cell output voltage Vs and the control target voltage for improvement of the pumping cell current control characteristics of the negative feedback loop. The PID controller 56 is further connected at an output terminal thereof to an inverting input terminal of the operational amplifier 32 via the switch SW2, the circuit terminal Pout, the resistor R2 and the circuit terminal Vcent so as to output the PID operation result to the operational amplifier 32. The output of the PID controller 56 is turned on and off by the switch SW2. The output terminal of the PID controller 56 is also connected to the circuit terminal COM via the resistors R1 and R2.

The operational amplifier 34 is connected to the circuit terminal Vcent via the switch SW1 so as to apply a reference voltage of 3.6 to the circuit terminal Vcent and to feed a small diagnosis current to the sensor element 10. The output of the operational amplifier 34 is turned on and off by the switch SW1.

The constant current source 46 is connected to the circuit terminal Vs+ via the switch SW5 so as to feed the constant current Icp through the sensing cell 24 and thereby keep the oxygen concentration of the reference gas chamber 26 constant as explained above. The output of the constant current source 46 is turned on and off by the switch SW5.

In the case where the measurement exhaust gas is fuel-rich, the concentration of oxygen in the measurement gas chamber 20 is lower than a stoichiometric air-fuel ratio level so that the output voltage Vs of the sensing cell 24 becomes higher than the control target voltage (450 mV). When the PID controller 56 performs PID operation on the difference ΔVs+ between the sensing cell output voltage Vs and the control target voltage, the operational amplifier 32 feeds the electric current Ip through the pumping cell 14 according to the PID operation result of the PD controller 56 in such a manner as to introduce a shortfall of oxygen into the measurement gas chamber 20 and adjust the oxygen concentration of the measurement gas chamber 20 to the stoichiometric air-fuel ratio level by the oxygen pumping action of the pumping cell 14. In the case where the measurement exhaust gas is fuel-lean, by contrast, the concentration of oxygen in the measurement gas chamber 20 is higher than the stoichiometric air-fuel ratio level so that the output voltage Vs of the sensing cell 24 becomes lower than the control target voltage value (450 mV). When the PID controller 56 performs PID operation on the difference ΔVs+ between the sensing cell output voltage Vs and the control target voltage, the operational amplifier 32 feeds the electric current Ip through the pumping cell 14 according to the PD operation result of the PID controller 56 in such a manner as to release an excess of oxygen from the measurement gas chamber 20 and adjust the oxygen concentration of the measurement gas chamber 20 to the stoichiometric air-fuel ratio level by the oxygen pumping action of the pumping cell 14. In this way, the direction and amount of flow of the pumping cell current Ip is controlled to maintain the potential difference Vs between the first and second electrodes 22 and 28 of the sensing cell 24 at the constant level (450 mV). The exhaust oxygen concentration can be thus determined by measuring the flow direction and amount of flow of the pumping cell current Ip.

The differential amplification circuit 57 is connected at input terminals thereof connected to the respective circuit terminals Vcent and Pout (although connection lines are omitted in the drawing) and at an output terminal thereof to the input port of the engine control unit 9 so as to read and amplify a voltage developed across the detection resistor R2 (i.e. a potential difference between the circuit terminals Vcent and Pout) by the passage of the pumping cell current Ip, i.e., convert the pumping cell current Ip to the oxygen concentration voltage signal, and then, output the resulting voltage signal to the engine control unit 9. The differential amplifier 57 may be connected to the engine control unit 9 via a signal transmission cable.

The oscillation inhibiting circuit 59 is arranged between the circuit terminals Vs+ and Ip+ and has a resistor R6 and a capacitor C4 connected in series to inhibit oscillations of the drive circuit 52.

The terminal voltage output circuit 54 is connected at input terminals thereof to the respective circuit terminals Vs+, COM and Ip+ (although connection lines are omitted in the drawing) and at an output terminal thereof to the control circuit 55 so as to read and output voltages at the respective circuit terminals Vs+, COM and Ip+ to the control circuit 55.

The diagnosis circuit 58 is also connected at input terminals thereof to the circuit terminals Vs+, COM and Ip+ (although connection lines are omitted in the drawing) and at an output terminal thereof to the control circuit 55 so as to read voltages developed at the respective circuit terminals Vs+, COM and Ip+ by the passage of the diagnosis current and, when any of the terminal voltages deviates from a normal range, detect the occurrence of a failure such as a short circuit in the electrical connection between the sensor element 10 and the sensor control unit 2.

Under normal conditions where the electrical connection between the sensor element 10 and the sensor control unit 2 through the terminal Vs+ (hereinafter referred to as "Vs+ connection") is proper, the voltage of the circuit terminal VS+ is held at 4.05 V, i.e., the sum of the common reference voltage (3.6V) of the circuit terminal COM and the output voltage Vs (450 mV) of the sensing cell 24. In the event that the Vs+ connection e.g. the electric wire 61 is shorted to a battery or ground potential for any reason, however, the voltage of the circuit terminal VS+ becomes equal to the battery or ground potential. This results in an excessive current flow to the sensor element 10 and thereby causes damage (e.g. cell blackening due to oxygen ion losses) to the sensor element 10. The diagnosis circuit 58 thus includes a first diagnosis section to compare the voltage of the circuit terminal VS+ with upper and lower threshold voltages and, when the voltage of the circuit terminal VS+ is higher than the upper threshold voltage or is lower than the lower threshold voltage, generate a high-level failure signal indicating the occurrence of the voltage failure in the Vs+ connection.

The voltage of the circuit terminal COM is held at 3.6 V (reference voltage) by the amplifier 32 under normal conditions where the electrical connection between the sensor element 10 and the sensor control unit 2 through the terminal COM (hereinafter referred to as "COM connection") is proper. In the event that the COM connection e.g. the electric wire 62 is shorted to a battery or ground potential for any reason, however, the voltage of the circuit terminal COM becomes equal to the battery or ground potential. This also results in an excessive current flow to the sensor element 10 and causes damage (e.g. cell blackening due to oxygen ion losses) to the sensor element 10. The diagnosis circuit 58 thus includes a second diagnosis section to compare the voltage of the circuit terminal COM with upper and lower threshold voltages and, when the voltage of the circuit terminal COM is higher than the upper threshold voltage or is lower than the lower threshold voltage, generate a high-level failure signal indicating the occurrence of the voltage failure in the COM connection.

The voltage of the circuit terminal Ip+ is also held at 3.6 V (reference voltage) under normal conditions where the electrical connection between the sensor element 10 and the sensor control unit 2 through the terminal Ip+ (hereinafter referred to as "Ip+ connection") is proper. In the event that the Ip+ connection e.g. the electric wire 63 is shorted to a battery or ground potential for any reason, however, the voltage of the circuit terminal Ip+ becomes equal to the battery or ground potential. This results in an excessive current flow to the sensor element 10 and causes damage (e.g. cell blackening due to oxygen ion losses) to the sensor element 10. The diagnosis circuit 58 thus a third diagnosis section to compare the voltage of the circuit terminal Ip+ with upper and lower threshold voltages and, when the voltage of the circuit terminal Ip+ is higher than the upper threshold voltage or is lower than the lower threshold voltage, generate a high-level failure signal indicating the occurrence of the voltage failure in the Ip+ connection.

In each of the first, second and third diagnosis sections, the upper and lower threshold voltages are set to predetermined voltage values. In the present embodiment, the upper threshold voltage is set to 9 V or set by subtracting a power supply voltage by a given value (e.g. 1.5 V) in view of fluctuations in power supply voltage. Further, the lower threshold voltage is set to e.g. 1 V in view of fluctuations in ground potential (0 V) in the present embodiment.

By the logical OR operation of the failure signals from the first, second and third diagnosis sections, the diagnosis circuit 58 sets a failure flag DIAG to notify the occurrence or non-occurrence of the voltage failure in the Vs+, COM or Ip+ connection and outputs the failure flag DIAG to the engine control unit 9 through the control circuit 55. The failure flag DIAG is set to "1" upon receipt of the failure signal from any of the first, second and third diagnosis sections, i.e., in the event of the sensor connection failure and reset to "0" under normal conditions.

The control circuit 55 is provided in the form of a microcomputer including a CPU, data/program storage memories such as RAM and ROM and signal input/output ports so as to perform total operation control of the sensor control unit 2 through the execution of various control processes. The control processes of the control circuit 55 includes a signal output process for outputting the oxygen concentration detection signal and the sensor resistance signal etc. to the engine control unit 9 and a mode control process for performing on-off control of the switches SW1 to SW5 under the control of the engine control unit 9 for energization mode control of the sensor element 10. The control circuit 55 is further configured to set a status flag indicating the current operating status of the sensor control unit 2 (notably, the operation mode of the sensor drive circuit 52) based on the operating conditions of the switches SW1 to SW5 and output the status flag to the engine control unit 9.

On the other hand, the engine control unit 9 performs integrated control of the sensor control unit 2 and the heater control unit 60 based on the inputs from the sensor control unit 2 through the execution of various control processes. The control processes of the engine control unit 9 include an exhaust oxygen concentration detection process for determining a detection value of the exhaust oxygen concentration according to the gas concentration detection signal from the differential amplification circuit 54, an air-fuel ratio control process for controlling the air-fuel ratio of the engine according to the exhaust oxygen concentration, a heater control process for controlling the heater control unit 60 to regulate the power supply to the heater 43, a diagnosis process for performing failure diagnosis to identify in which of the Vs+, COM and Ip+ connections the voltage failure is occurring and the cause or nature of the sensor connection failure according to the failure flag DIAG from the diagnosis circuit 58, the circuit terminal voltage signals from the terminal voltage output circuit 54 and various failure identification parameters and a mode control process for generating a mode command for energization mode control of the sensor element 10. In the present embodiment, the engine control unit 9 is provided in the form of a microcomputer including a CPU, data/program storage memories such as RAM and ROM and signal input/output ports to execute the respective control processes according to programs stored in the memories by reflecting the input signals through the content of the input port register and outputting the content of the output port register as the output signals.

Figure 3:
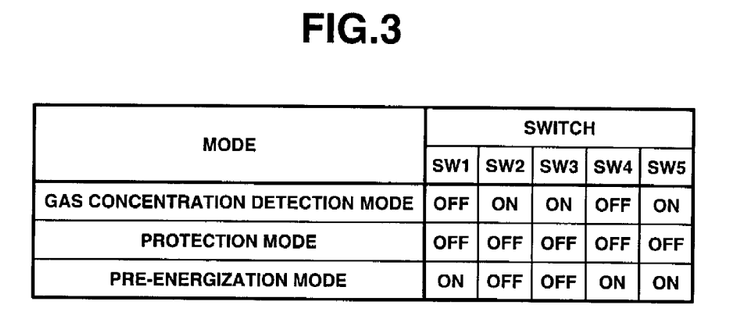
FIG. 3 is a logic diagram showing the operating conditions of mode selection switches of the electronic control device according one embodiment of the present invention.

The energization mode of the sensor element 10 (the pumping cell 14 and the sensing cell 24), i.e., the operation mode of the sensor drive circuit 52 is generally selected from a plurality of modes including at least a gas concentration detection mode, a protection mode and a pre-energization mode. In the present embodiment, the sensor drive circuit 52 is switched among three modes: a gas concentration detection mode, a protection mode and a pre-energization mode. The operating conditions of the respective switches SW1 to SW5 in each mode are indicated in FIG. 3.

The gas concentration detection mode is selected to provide a relatively large current supply to the sensor element 10 (the pumping cell 14 and the sensing cell 24) for exhaust oxygen concentration detection and engine combustion control. Upon selection of the gas concentration detection mode, the engine control unit 9 outputs electrical signals as the mode command to the sensor drive circuit 52 so as to turn on the switches SW2, SW3 and SW5 and turn off the switches SW1 and SW4. With this, the electrical continuity between the sensor element 10 and the sensor drive circuit 52 is established to feed the electric currents Ip and Icp through the pumping cell 14 and the sensing cell 24, respectively. At this time, the flow direction and amount of the pumping cell current Ip through the pumping cell 14 is controlled in such a manner as to keep the potential difference Vs of the sensing cell 24 at the constant level as explained above. The maximum allowable energization current of the pumping cell 14 is determined depending on the current drive performance of the operational amplifiers 32 and 36 and is set to e.g. about 20 mA.

The protection mode is selected to provide electrical protection to the sensor element 10 in the event of the voltage failure in any of the electrical connections between the sensor element 10 and the sensor control unit 2. Upon selection of the protection mode, the engine control unit 9 outputs electrical signals as the mode command to the sensor drive circuit 52 so as to turn off all of the switches SW1 to SW5. The electrical continuity between the sensor element 10 and the sensor drive circuit 52 is then interrupted so that the sensor element 10 receives no inputs from the operational amplifiers 32, 34 and 36 and the constant current source 46. Namely, the sensor element 10 is de-energized and electrically protected from damage caused by a continuous, abnormal current flow even in the event of the sensor connection failure.

The pre-energization mode is selected to pre-energize at least one of the pumping cell 14 and the sensing cell 24 (in the present embodiment, the pumping cell 14) and thereby activate the sensor element 10 in readiness for the gas concentration detection mode. Upon selection of the pre-energization mode, the engine control unit 9 outputs electrical signals as the mode command to the sensor drive circuit 52 so as to turn on the switches SW1, SW4 and SW5 and turn off the switches SW2 and SW3. When the switches SW2 and SW3 are turned off, the negative feedback loop of the sensor drive circuit 52 is interrupted such that the sensor element 10 receives no inputs from the operational amplifiers 32 and 36. Namely, the current feedback control of the pumping cell 14 is stopped during the pre-energization mode. When the switches SW1, SW4 and SW5 are turned on, the sensor element 10 receives a relatively small current supply from the operational amplifier 34, the constant current source 46 and the voltage divider 65. The constant current Icp is fed through the sensing cell 24 to accumulate a substantially constant concentration of oxygen in the reference gas chamber 26 by the oxygen pumping action of the sensing cell 24. Further, the diagnosis circuit 58 performs failure diagnosis to judge the occurrence or nonoccurrence of the sensor connection failure by the passage of the diagnosis current. In this way, the sensor element 10 is supplied with a relatively small amount of electric current during the pre-energization mode. This makes it possible to prevent an excessive current flow to the sensor element 10 and protect the sensor element 10 from damage (e.g. cell blackening) caused by such an excessive current flow even in the event of the sensor connection failure. This also makes it possible to diagnose the sensor connection failure during the pre-energization mode without causing damage to the sensor element 10.

It is herein conceivable that the sensor drive circuit 52 may directly switch over to the gas concentration detection mode. In such a case, however, there arises an abnormal current flow from the sensor drive circuit 52 to the sensor element 10 by the switchover of the sensor drive circuit 52 to the gas concentration detection mode in the event of the sensor connection failure. For example, if the electric wire 62 is short-circuited to a ground potential, a current line is developed from the operational amplifier 32 to the ground via the pumping cell 14 and the electric wire 62 so as to cause a flow of the maximum current output of the operational amplifier 32 to the pumping cell 14. This results in damage (cell blacking etc.) to the sensor element 10 in a short time.

In order to prevent such an abnormal, excessive current flow to the sensor element 10 and protect the sensor element 10 from damage, the electronic control device 5 is so configured that the sensor drive circuit 52 switches over to the gas concentration detection mode only from the pre-energization mode. More specifically, the switchover of the sensor drive circuit 52 to the gas concentration detection mode is prohibited by satisfaction of a certain prohibition condition where the sensor drive circuit 52 is not in the pre-energization mode (but in any other mode e.g. protection mode) at the time of receipt of the mode command to specify the gas concentration detection mode. The sensor drive circuit 52 does not switches over to the gas concentration detection mode immediately upon receipt of the mode command, but switches over to the gas concentration detection mode by receipt of the mode command and by unsatisfaction of the prohibition condition (e.g. when the mode command is to specify any mode other than the gas concentration detection mode or when the sensor drive circuit 52 is already in the pre-energization mode at the time of receipt of the mode command). The sensor element 10 receives a small current output from the sensor drive circuit 52 during the pre-energization mode regardless of whether, for example, the electric wire 62 is short-circuited to a ground potential to develop a current line from the voltage divider 65 to the ground via the pumping cell 14 and the electric wire 62. Then, the sensor drive circuit 52 switches over to the protection mode rather than the gas concentration detection mode upon detection of the sensor connection failure. It is therefore possible to prevent an abnormal, excessive current flow to the sensor element 10 and protect the sensor element 10 from damage assuredly even in the event of the sensor connection failure.

The energization control of the sensor element 10 is carried out by the following procedure through the execution of the mode control processes of the engine control unit 9 and the sensor control circuit 55 in the present embodiment.

The engine control unit 9 and the sensor control circuit 55 becomes actuated and initialized upon power-on of the engine control system 1. After the initialization of internal variables, the engine control unit 9 and the sensor control circuit 55 start their respective mode control processes.

The engine control unit 9 first makes a mode selection by judging the current operating status of the sensor element 10 based on the sensor resistance signal and by judging the occurrence or nonoccurrence of the sensor connection failure based on the failure flag DIAG. When the sensor element 10 is judged as already being in the active state, the engine control unit 9 selects the gas concentration detection mode. The engine control unit 9 selects the pre-energization mode when the sensor element 10 is judged as not being in the active state e.g. immediately after the start-up of the sensor element 10. The engine control unit 9 selects the protection mode in the event of the sensor connection failure. When the sensor connection failure is resolved, the engine control unit 9 selects the appropriate sensor energization mode by judging the current operating status of the sensor element 10 based on the sensor resistance signal.

The engine control unit 9 next generates the mode command to specify one of the sensor energization modes according to the result of the mode selection, and then, outputs the mode command to the sensor control circuit 55. In the present embodiment, the mode command is outputted through a mode command output subroutine shown in FIG. 4.

Figure 4:
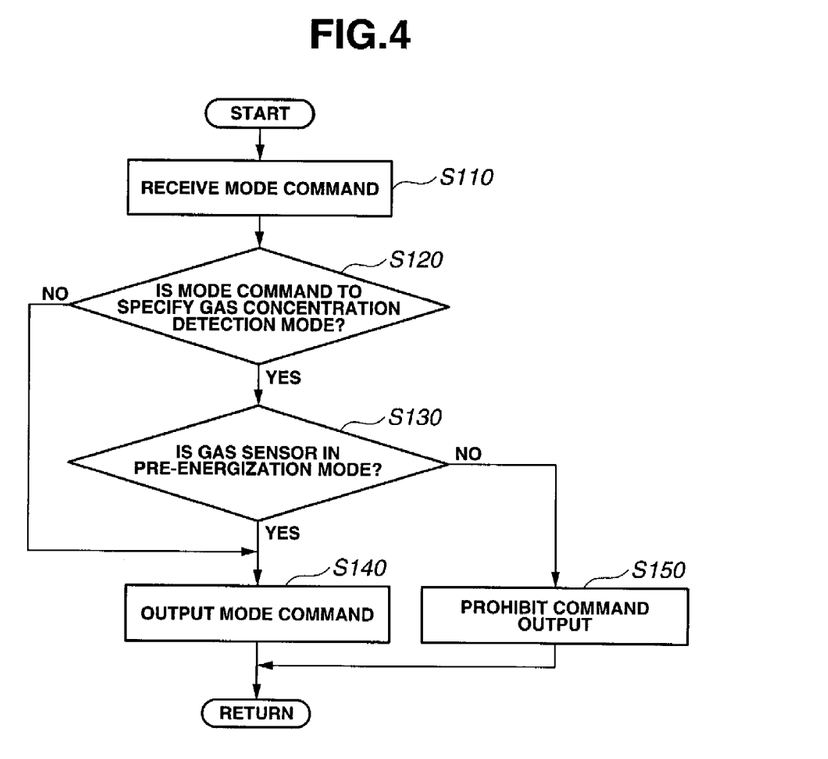
FIG. 4 is a flowchart for a mode command output program of the electronic control device according one embodiment of the present invention.

At step S10, the engine control unit 9 shifts from the main process routine to the mode command output subroutine and receives the mode command.

At step S120, the engine control unit 9 judges whether the mode command is to specify the gas concentration detection mode. If Yes at step S120, the program control proceeds to step S130. If No at step S120, the program control proceeds to step S140.

At step S130, the engine control unit 9 retrieves the status flag from the from the sensor control unit 2 and judges based on the status flag whether the sensor drive circuit 52 is currently in the pre-energization mode. If Yes at step S130, the program control proceeds to step S140. If No at step S130, the program control proceeds to step S150.

At step S140, the engine control unit 9 outputs the switch control signals as the mode command to the sensor control unit 2 via the transmission cable 71 so as to switch the sensor drive circuit 52 into the gas concentration detection mode by on-off control of the mode selection switches SW1 to SW5.

At step S150, the engine control unit 9 disables the output of the mode command so as to prohibit the mode switchover and maintain the current energization mode of the sensor element 10.

After step S140 or S150, the program control returns to the main process routine of the mode control process.

On the other hand, the sensor control circuit 55 turns on and off the mode selection switches SW1 to SW5 under the mode command from the engine control unit 9 in the mode control process.

Figure 5:
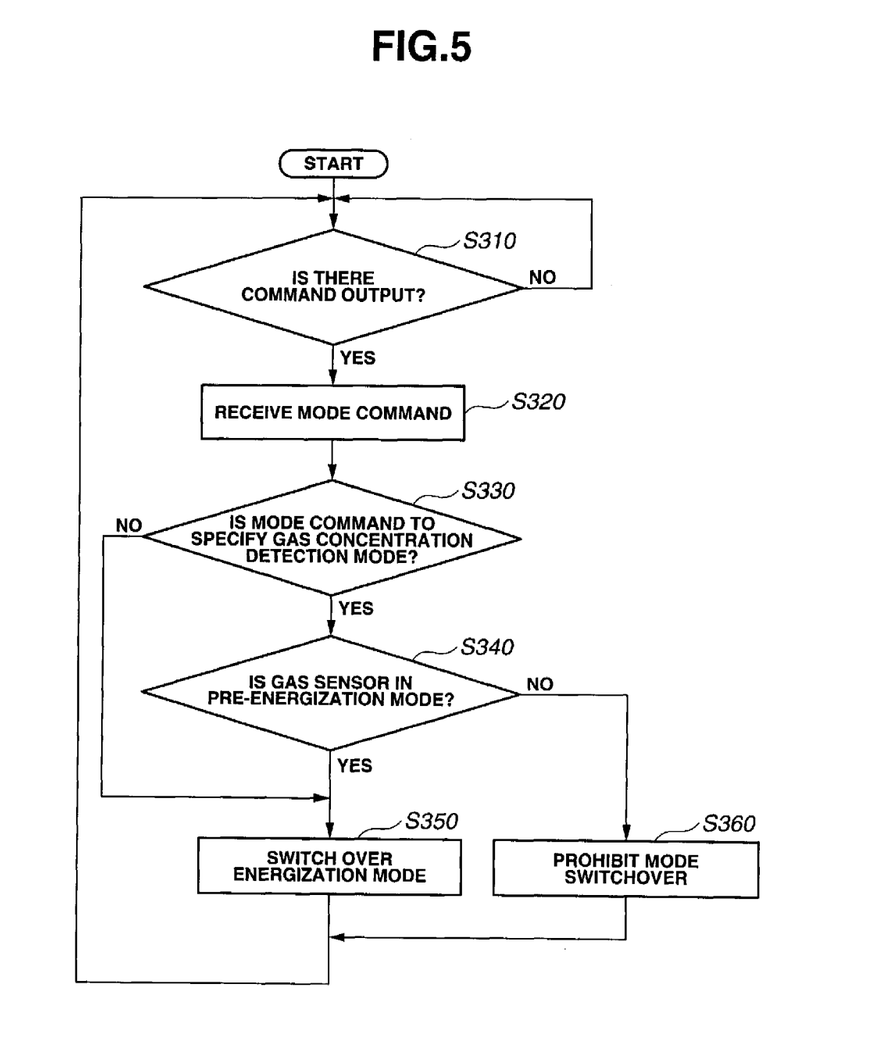
FIG. 5 is a flowchart for a mode command processing program of the electronic control device according to one embodiment of the present invention.

In the present embodiment, the mode selection switches SW1 to SW5 are operated through a mode command processing subroutine shown in FIG. 5.

At step S310, the sensor control circuit 55 judges whether there is output of the mode command from the engine control unit 9, i.e., whether the switch control signals (electrical signals) are transmitted from the engine control unit 9 through the transmission cable 71. If Yes at step S310, the program control proceeds to step S320. If No at step S310, the program control repeats this step until detection of the mode command output.

At step S320, the sensor control circuit 55 receives the mode command from the engine control unit 9.

At step S330, the sensor control circuit 55 judges whether the mode command is to specify the gas concentration detection mode. If Yes at step S330, the program control proceeds to step S340. If No at step S330, the program control proceeds to step S350.

At step S340, the sensor control circuit 55 judges whether the sensor drive circuit 52 is currently in the pre-energization mode based on the operating conditions of the switches SW1 to SW5. If Yes at step S340, the program control proceeds to step S350. If No at step S340, the program control proceeds to step S360.

At step S350, the sensor control circuit 55 turns on or off the switches SW1 to SW5 according to the switch control signals so as to switch the operation mode of the sensor drive circuit 52 according to the mode command.

At step S360, the sensor control circuit 55 disables the on-off control of the mode selection switches SW1 to SW2 so as to prohibit the mode switchover and maintain the current energization mode of the sensor element 10.

After step S350 or S360, the program control returns to step S310 and repeats steps S310 to S360 until the sensor control unit 2 becomes stopped.

As described above, the electronic control device 5 functions as a gas sensor control device that prohibits the switchover of the sensor drive circuit 52 to the gas concentration detection mode by disabling the output of the mode command and by disabling the on-off control of the mode selection switches SW1 to SW5 by satisfaction of the prohibition condition (i.e. by affirmative judgment in step S120 and negative judgment in step S130 and by affirmative judgment in step S330 and negative judgment in step S340) and allows the switchover of the sensor drive circuit 52 to the gas concentration detection mode only from the pre-energization mode. This makes it possible to prevent an abnormal, excessive current flow to the sensor element 10 and protect the sensor element 10 from damage assuredly even in the event of the sensor connection failure.

In the present embodiment, the electronic control device 5 includes two separate control units 2 and 9 connected by the signal transmission cable 71. The first control unit 9 has a first receiving section or means to receive the mode command, a first judging section or means to judge satisfaction of the prohibition condition and a first prohibiting section or means to prohibit the sensor element 10 from switching over to the gas concentration detection mode upon satisfaction of the prohibition condition. The second control unit 2 has a second receiving section or means (the control circuit 55) to receive the mode command, a second judging section or means (the control circuit 55) to judge satisfaction of the prohibition condition, a switchover section or means (the sensor drive circuit 52) connected with the sensor element 10 to make a switchover of the sensor element 10 into the appropriate energization mode according to the mode command and a second prohibiting section or means (the control circuit 55) to prohibit the sensor element 10 from switching over to the gas concentration detection mode upon satisfaction of the prohibition condition. The electronic control device 5 is thus able to double-check whether the prohibition condition is satisfied and to prohibit the sensor drive circuit 52 from mistakenly switching over to the gas concentration detection mode even when the engine control unit 9 outputs the mode command by misjudging that the prohibition condition is satisfied or when the sensor control unit 2 receives the mode command under the influence of noise etc. This makes it possible to prevent an abnormal, excessive current flow to the sensor element 10 and protect the sensor element 10 from damage more assuredly in the event of the sensor connection failure. The arrangement of the second judging section or means and switchover section or means in the control unit 2 is particularly effective in prohibiting the sensor element 10 from mistakenly switching over to the gas concentration detection mode due to misjudgment of the prohibition condition or under the influence of noise etc. and thereby protecting the sensor element 10 from damage caused by an abnormal, excessive current flow in the event of the sensor connection failure.

The entire contents of Japanese Patent Application No. 2006-248100 (filed on Sep. 13, 2006) are herein incorporated by reference.

Although the present invention has been described with reference to the above-specific embodiments of the invention, the invention is not limited to the these exemplary embodiments. Various modification and variation of the embodiments described above will occur to those skilled in the art in light of the above teaching. For example, the electronic control device 5 may have a judging section or means and a prohibiting section or means in either the engine control unit 9 or the sensor control unit 2 so as to judge satisfaction of the prohibition condition only once although two judging sections are provided in the respective control units 2 and 9 in the above embodiment. Alternatively, the electronic control device 5 may be configured to judge satisfaction of the prohibition condition three or more times. Further, the electronic control device 5 may alternatively establish four or more energization modes by e.g. setting a pre-energization mode and a diagnosis mode separately. The scope of the invention is defined with reference to the following claims.

What is claimed is:

1. A control method for a gas sensor, the gas sensor having a sensor element formed with at least one electrochemical cell to detect the concentration of a specific gas component in measurement gas, the control method comprising:
   receiving a mode command to specify one of a plurality of sensor energization modes including at least a gas concentration detection mode, a protection mode and a pre-energization mode;
   switching the sensor element into said one of the plurality of sensor energization modes according to the mode command;
   judging satisfaction of a certain condition where the mode command is to specify the gas concentration detection mode and the sensor element is in any of the plurality of sensor energization modes other than the pre-energization mode at the time of receipt of the mode command; and
   at the time of receipt of the mode command specifying switching of the electrochemical cell of the sensor element to the gas concentration detection mode, prohibiting the sensor element from switching over to the gas concentration detection mode if the sensor element is in the protection mode and switching the sensor element to the gas concentration detection mode if the sensor element is in the pre-energization mode.

2. A control device for a gas sensor, the gas sensor having a sensor element formed with at least one electrochemical cell to detect the concentration of a specific gas component in measurement gas, the control device comprising:
   receiving means for receiving a mode command to specify one of a plurality of sensor energization modes including at least a gas concentration detection mode, a protection mode and a pre-energization mode;
   switchover means for switching the electrochemical cell of the sensor element into said one of the plurality of sensor energization modes according to the mode command;
   judging means for judging satisfaction of a certain condition where the mode command is to specify the gas concentration detection mode and the electrochemical cell of the sensor element is in any of the plurality of sensor energization modes other than the pre-energization mode at the time of receipt of the mode command; and
   prohibiting means for prohibiting the sensor element from switching over to the gas concentration detection mode when the certain condition is satisfied,
   wherein at the time of receipt of the mode command specifying switching of the electrochemical cell of the sensor element to the gas concentration detection mode, the switchover means switches to the gas concentration detection mode from the pre-energization mode and does not switch to the gas concentration detection mode from the protection mode.

3. The control device according to claim 1,
   the sensor element having a sensing cell and a pumping cell as said one electrochemical cell and a measurement gas chamber defined between the sensing cell and the pumping cell so that the measurement gas chamber is in communication with the outside of the gas sensor through a gas diffusion material;
   the sensing cell having a solid electrolyte material body and a pair of first and second sensing cell electrodes arranged on opposite sides of the solid electrolyte material body, with the first sensing cell electrode being exposed to the measurement gas chamber, so as to develop a voltage between the first and second sensing cell electrodes according to the concentration of oxygen in the measurement gas chamber; and
   the pumping cell having a solid electrolyte material body and a pair of first and second pumping cell electrodes arranged on opposite sides of the solid electrolyte material body, with the second pumping cell electrode being exposed to the measurement gas chamber, so as to cause pumping of oxygen in the measurement gas chamber by the passage of an electric current between the first and second pumping cell electrodes.

4. The control device according to claim 2,
   wherein the judging means judges whether the sensor element is in the pre-energization mode at the time of receipt of the mode command specifying switching of the sensor element to the gas concentration detection mode; and
   wherein the prohibiting means prohibits the sensor element from switching over to the gas concentration detection mode if the judging means judges that the sensor element is not in the pre-energization mode at the time of receipt of the mode command specifying switching of the sensor element to the gas concentration detection mode.

5. The control device according to claim 1,
   the control device comprising separate first and second control units and a signal transmission unit arranged between the first control unit and the second control unit to transmit electric signals as the mode command;
   each of the first and second control units having a receiving section as said receiving means to receive the mode command;
   the second control unit having a switchover section as said switchover means connected with the sensor element to make a mode switchover of the sensor element according to the mode command;
   at least one of the first and second control units having a judging section as said judging means to judge whether the certain condition is satisfied and a prohibiting section as said prohibiting means to prohibit the switchover of the sensor element to the gas concentration detection mode when the certain condition is satisfied.

6. The control device according to claim 5, the second control unit having both of the judging section and the switchover section.

7. The control device according to claim 2,
the gas sensor having a heater for heating the sensor element; and
the control device further comprising a heater control unit connected to the heater to control the heater.

8. The control device according to claim 7,
wherein the judging means judges whether the sensor element is in the pre-energization mode at the time of receipt of the mode command specifying switching of the sensor element to the gas concentration detection mode; and
wherein the prohibiting means prohibits the sensor element from switching over the gas concentration detection mode if the judging means judges that the sensor element is not in the pre-energization mode at the time of receipt of the mode command specifying switching of the sensor element to the gas concentration detection mode.

9. A control device for a gas sensor, the gas sensor having a sensor element formed with at least one electrochemical cell to detect the concentration of a specific gas component in measurement gas, the control device comprising:
a sensor control circuit; and
a sensor drive circuit,
wherein the sensor control circuit is configured to:
receive a mode command to specify one of a plurality of sensor energization modes including at least a gas concentration detection mode, a protection mode and a pre-energization mode;
determine whether the received mode command is for specifying the gas concentration detection mode;
judge, in response to determining that the received mode command specifies switching to the gas concentration detection mode, whether the sensor drive circuit is in a pre-energization mode; and
prohibit the sensor drive circuit from switching over to the gas concentration detection mode if it is judged that the sensor element is not in a pre-energization mode.

10. A gas sensor system, comprising:
a gas sensor having a sensor element formed with at least one electrochemical cell to detect the concentration of a specific gas component in measurement gas; and
a control device for the gas sensor, the control device comprising:
means for receiving a mode command to specify one of a plurality of sensor energization modes including at least a gas concentration detection mode, a protection mode and a pre-energization mode;
switchover means for switching the electrochemical cell of the sensor element into said one of the plurality of sensor energization modes according to the mode command;
judging means for judging satisfaction of a certain condition where the mode command is to specify the gas concentration detection mode and the electrochemical cell of the sensor element is in any of the plurality of sensor energization modes other than the pre-energization mode at the time of receipt of the mode command; and
prohibiting means for prohibiting the sensor element from switching over to the gas concentration detection mode when the certain condition is satisfied,
wherein at the time of receipt of the mode command specifying switching of the electrochemical cell of the sensor element to the gas concentration detection mode, the switchover means switches to the gas concentration detection mode from the pre-energization mode and does not switch to the gas concentration detection mode from the protection mode.

* * * * *